United States Patent

Metcalf et al.

[11] 4,100,349
[45] Jul. 11, 1978

[54] α-ACETYLENIC DERIVATIVES OF HISTAMINE AND RELATED COMPOUNDS

[76] Inventors: Brian Walter Metcalf, 8, avenue du General de Gaulle, 67000 Strasbourg; Michel Jung, 1, rue des Dahlias, 67400 Illkirch Graffenstaden, both of France

[21] Appl. No.: 812,266

[22] Filed: Jul. 1, 1977

[51] Int. Cl.$^2$ .................................... C07D 233/64
[52] U.S. Cl. .................. 548/337; 424/273 R; 544/28; 548/342
[58] Field of Search .................. 548/337, 342, 344

[56] References Cited

U.S. PATENT DOCUMENTS

| 3,169,971 | 2/1965 | Sletzinger et al. | 548/344 |
| 3,387,031 | 6/1968 | Johnson et al. | 548/344 |

FOREIGN PATENT DOCUMENTS

| 715,182 | 9/1954 | United Kingdom | 548/342 |

*Primary Examiner*—Natalie Trousof
*Attorney, Agent, or Firm*—L. Ruth Hattan; Eugene O. Retter; George W. Rauchfuss, Jr.

[57] ABSTRACT

Novel acetylenic derivatives of amines of the following general structure

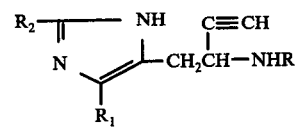

wherein R is hydrogen, alkylcarbonyl wherein the alkyl moiety has from 1 to 4 carbon atoms and is straight or branched, alkoxycarbonyl wherein the alkoxy moiety has from 1 to 4 carbon atoms and is straight or branched or

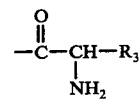

wherein $R_3$ is hydrogen, a straight or branched lower alkyl group of from 1 to 4 carbon atoms, benzyl or p-hydroxybenzyl; each of $R_1$ and $R_2$ is hydrogen, halogen selected from fluorine, chlorine, bromine and iodine or a straight or branched lower alkyl group of from 1 to 4 carbon atoms and may be the same or different with the proviso that when both $R_1$ and $R_2$ are halogen $R_1$ and $R_2$ are the same; and pharmaceutically acceptable salts and individual optical isomers thereof.

9 Claims, No Drawings

# α-ACETYLENIC DERIVATIVES OF HISTAMINE AND RELATED COMPOUNDS

FIELD OF INVENTION

This invention relates to novel pharmaceutically useful acetylenic derivatives of histamine and related compounds.

BACKGROUND OF INVENTION

Most mammalian tissue contains histamine, concentration being particularly high in the skin, intestinal mucosa and the lungs. Every mammalian tissue that contains histamine, including white blood cells, appears capable of synthesizing the amine from histidine. The principal enzyme involved in catalyzing in vivo the conversion of histidine to histamine is histidine decarboxylase which is specific for the substrate L-histidine. In many tissues the chief storage site of histamine is the mast cell, or in the case of blood, the basophil which is the circulating counterpart of the fixed-tissue mast cell. Mast cells are not the only tissue source of histamine which is present in substantial amounts in the human epidermis, the central nervous system and the gastrointestinal mucosa.

Histamine is involved in various physiological processes. Histamine is released during the antigen-antibody reaction and is responsible, in large part, for the hypersensitivity reaction characterized by vasodilation, itching and edema formation. This type of antigen-antibody reaction wherein the principal cells involved are mast cells and basophils from which histamine is released is commonly referred to as an immediate hypersensitivity reaction. In addition to antigens, or allergens, histamine is released by many chemical substances, macromolecules, venoms, physical insult, such as heat and other injurious stimuli. Gastric acid secretion is known to be stimulated by histamine. Also, histamine is known to be frequently involved in initiation of sensory impulses evoking pain and itching. It has also been found that histamine levels are high in many tissues undergoing rapid growth, for example, embryonic tissue, regenerating liver and malignant growths.

Correlations between levels of histamine and histidine decarboxylase activity in tissues have been made. In the brain which contains histamine and histidine decarboxylase the turnover of histamine is rapid being augmented by stressful stimuli that also increases histidine decarboxylase activity. Inhibitors of L-histidine decarboxylase, such as, α-hydrazinohistidine are known to lower histamine concentrations. In rat fetal tissue, wherein high levels of histamine are present, it has been shown that inhibition of L-histidine decarboxylase arrests fetal development.

The effects of histamine and its mode of action are well documented. It is believed that the amine exerts its effect through at least two receptors being classified as $H_1$ and $H_2$ receptors. Several agents are known to counter the effects of histamine, however, not all such agents prevent the formation of histamine. For example, classical antihistamines useful in treating allergic reactions are believed to exert their utility by interfering with the binding of histamine with $H_1$ receptors. Similarly agents useful in countering the stimulant effect of histamine on gastric acid secretion are believed to operate by interfering with the binding of histamine with $H_2$ receptors.

Agents capable of blocking $H_1$ receptors find use in treating acute exudative types of allergy, such as, seasonal rhinitis, hay fever, pollinosis relieving the sneezing, rhinorrhea, itching eyes, nose and throat. Such agents are also useful in controlling cough and to a degree find use in treating systemic anaphylaxis and bronchial asthma. Antihistamine agents which act through $H_1$ receptors are also useful in treating allergic dermatoses, such as acute and chronic urticaria, angioedema, itching pruritides, for example, atopic dermatitis and contact dermatitis, in the control of urticarial and edematous lesions of serum sickness, control of blood transfusion reactions and control of drug reactions attributable to allergic phenomena. Agents which block $H_2$ receptors are useful in treating peptic ulceration, the Zollinger-Ellison syndrome and other gastric hypersecretory states.

Agents which block the formation of histamine by inhibiting the activity of histidine decarboxylase, for example, α-methylhistidine and α-hydrazinohistidine, are reported to be useful in the same manner as antihistaminic agents that are blockers of $H_1$ and $H_2$ receptors. Additionally histidine decarboxylase inhibitors are implicated as being useful in the control of certain tumors which are high in histamine content.

The compounds of the present invention prevent the formation of histamine by inhibiting the action of histidine decarboxylase rendering said compounds useful in treating pathophysiological conditions which result from histamine. The presently claimed compounds can be used in the same manner and for the same purposes as are compounds that antagonize $H_1$ and $H_2$ receptors.

SUMMARY OF INVENTION

The compounds of the present invention are represented by the following general Formula I:

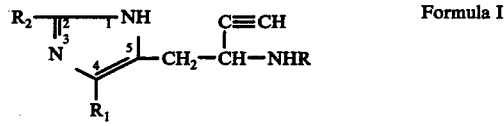

Formula I

In the above general Formula I R is hydrogen, alkylcarbonyl wherein the alkyl moiety has from 1 to 4 carbon atoms and is straight or branched, alkoxycarbonyl wherein the alkoxy moiety has from 1 to 4 carbon atoms and is straight or branched or

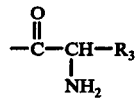

wherein $R_3$ is hydrogen, a straight or branched lower alkyl group of from 1 to 4 carbon atoms, benzyl or p-hydroxybenzyl; each of $R_1$ and $R_2$ is hydrogen, halogen selected from fluorine, chlorine, bromine and iodine or a straight or branched lower alkyl group of from 1 to 4 carbon atoms and may be the same or different with the proviso that when $R_1$ and $R_2$ are halogen $R_1$ and $R_2$ are the same.

The pharmaceutically acceptable salts and individual optical isomers of the compounds of general Formula I are also included within the scope of this invention.

DETAILED DESCRIPTION OF INVENTION

Illustrative examples of straight chain or branched chain lower alkyl groups of from 1 to 4 carbon atoms in the above general Formula I are methyl, ethyl, n-propyl, isopropyl, n-butyl and tert-butyl.

As used in general Formula I the term alkyl carbonyl is taken to mean the group

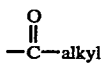

wherein the alkyl group is straight or branched and has from 1 to 4 carbon atoms, for example, methyl, ethyl, n-propyl, isopropyl, n-butyl and tert-butyl.

As used in general Formula I the term alkoxycarbonyl is taken to mean the group

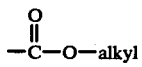

wherein the alkoxy group, that is, -O-alkyl has from 1 to 4 carbon atoms and is straight or branched, for example, methoxy, ethoxy, n-propoxy, isopropoxy, n-butoxy and tert-butoxy.

Illustrative examples of pharmaceutically acceptable salts of the compounds of this invention include non-toxic acid addition salts formed with inorganic acids, such as, hydrochloric, hydrobromic, sulfuric and phosphoric acid, and organic acids, such as, methane sulfonic, salicylic, maleic, cyclamic, malonic, tartaric, citric and ascorbic acids. The salts are prepared by conventional means.

Preferred compounds of this invention are those of general Formula I wherein R is hydrogen or alkyl carbonyl wherein the alkyl moiety is straight or branched and has from 1 to 4 carbon atoms with compounds wherein R is hydrogen being more preferred. Another preferred embodiment of this invention is compounds of general Formula I wherein each of $R_1$ and $R_2$ is hydrogen, halogen or methyl with compounds wherein each of $R_1$ and $R_2$ is hydrogen, chlorine, fluorine or methyl being more preferred. The most preferred compound of this invention is that of general Formula I wherein R is hydrogen and each of $R_1$ and $R_2$ is hydrogen.

Illustrative examples of compounds of the present invention are the following:

1-acetylene-2-(5-imidazolyl)ethylamine,
1-acetylene-2-[5-(4-fluoro)imidazolyl]ethylamine,
1-acetylene-2-[5-(4-chloro)imidazolyl]ethylamine,
1-acetylene-2-[5-(2,4-difluoro)imidazolyl]ethylamine,
1-acetylene-2-[5-(2,4-dibromo)imidazolyl]ethylamine,
1-acetylene-2-[5-(4-methyl)imidazolyl]ethylamine,
1-acetylene-2-[5-(2-fluoro-4-methyl)imidazolyl]ethylamine,
1-acetylene-2-[5-(2,4-dimethyl]imidazolyl]ethylamine,
1-acetylene-2-[5-(2,4-diethyl)imidazolyl]ethylamine,
1-acetylene-2-[5-(2,4-diisopropyl)imidazolyl]ethylamine,
1-acetylene-2-[5-(2,4-di-tert-butyl)imidazolyl]ethylamine,
1-acetylene-2-[5-(2-butyl)imidazolyl]ethylamine,
1-acetylene-2-[5-(2-iodo)imidazolyl]ethylamine,
N-[1-acetylene-2-[5-(2-fluoro)imidazolyl]ethyl]acetamide,
N-[1-acetylene-2-(5-imidazolyl)ethyl]methyl carbamate,
N-[1-acetylene-2-[5-(2-ethyl)imidazolyl]ethyl]-2-aminopropionamide and
N-[1-acetylene-2-(5-imidazolyl)ethyl]-2-amino-3-phenylpropionamide.

The compounds of Formula I are irreversible inhibitors of histidine decarboxylase, the enzyme which in vivo converts histidine to histamine. Thus the compounds block the formation of histamine which is known to play an important role in certain patho-physiological conditions. As inhibitors of histidine decarboxylase the compounds of the present invention are useful in the same manner as any known antihistiminic agent whether such agent exerts its effectiveness by blocking $H_1$ or $H_2$ receptors or other means. The compounds of this invention are useful in treating the patho-physiological conditions due to histamine. Thus, the compounds of general Formula I have many utilities being useful in treating acute exudative types of allergy, such as, seasonal rhinitis, hay fever, and pollinosis relieving the sneezing, rhinorrhea, itching eyes, nose and throat. The compounds of general Formula I are also useful in controlling cough and in treating systemic anaphylaxis and bronchial asthma, and are useful as broncholdilators. Also, the compounds of general Formula I are useful in treating allergic dermatoses, such as, acute urticaria, chronic urticaria, angioedema, itching pruritides, for example, atopic dermatitis and contact dermatitis. The compounds of general Formula I are also useful in treating urticarial and edematous lesions of serum sickness, blood transfusion reactions attributable to allergic phenomena and nausea. The compounds of general Formula I are also useful in treating peptic ulceration, the Zollinger-Ellison syndrome and other gastric hypersecretory states. As described hereinabove it has been found that histamine levels are high in rapidly growing tissues, such as, tumors, hence, the compounds of general Formula I by inhibiting the formation of histamine, may be useful in controlling the growth of certain tumors, for example, Walker mammary carcinoma and Erlich ascitic tumors.

The compounds of this invention can be administered in various manners to achieve the desired effect. The compounds can be administered alone or in the form of pharmaceutical preparations to the patient being treated either orally, parenterally, that is, subcutaneously, intravenously or intrperitoneally, or topically. The compounds can be administered by intranasal instillation or by application to mucous membranes such as that of the nose, throat and bronchial tubes, for example, in an aerosol spray containing small particles of a novel compound of this invention in a spray solution or dry powder form.

The amount of novel compound administered will vary and can be any effective amount. Depending on the patient, the condition being treated and the mode of administration, the quantity of novel compound administered may vary over a wide range to provide as an effective amount in a unit dosage form of from about 0.1 to 500 mg/kg (milligrams per kilogram) of body weight of the patient per dose and preferably from about 50 to 200 mg/kg to achieve the desired effect. For example, the desired effect can be obtained by consumption of a unit dosage form, such as, for example, a tablet containing from 10 to 500 mg of a novel compound of this invention taken 1 to 4 times daily.

As used herein the term patient is taken to mean warm blooded animals such as birds and mammals, for example, cats, dogs, rats, mice, guinea pigs, sheep, horses, bovine cows and humans.

The solid unit dosage forms can be of the conventional type. Thus, the solid form can be a capsule which can be of the ordinary gelatin type containing a novel compound of this invention and a carrier, for example, lubricant and inert fillers such as lactose, sucrose and corn starch. In another embodiment, the novel compounds are tableted with conventional tablet bases such as lactose, sucrose or corn starch in combination with binders such as acacia, corn starch or gelatin, disintegrating agents such as corn starch, potato starch, or alginic acid, and a lubricant such as stearic acid, or magnesium stearate.

For parenteral administration the compounds may be administered as injectable dosages of a solution or suspension of the compound in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of petroleum, animal, vegetable or synthetic origin, for example, peanut oil, soybean oil, and mineral oil. In general water, saline, aqueous dextrose, and related sugar solutions, ethanols and glycols such as propylene glycol or polyethylene glycol are preferred liquid carriers, particularly for injectable solutions.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber manufactured by the Dow-Corning Corporation.

For use as aerosols the novel compounds in solution or suspension may be packaged in a pressurized aerosol container together with a gaseous or liquefied propellant, for example, dichlorodifluoromethane, dichlorodifluoromethane with dichlorodifluoroethane, carbon dioxide, nitrogen or propane, with the usual adjuvants such as cosolvents, and wetting agents, as may be necessary or desirable. The compounds may also be administered in a non-pressurized form such as in a nubulizer or atomizer.

The utility of the compounds of general Formula I as irreversible inhibitors of histidine decarboxylase may be demonstrated as follows. A compound of general Formula I is administered as an aqueous solution or suspension to rats or mice either orally or parenterally. At different time intervals after administration of the test compound the animals are injected intraperitoneally with 2 μCi of 2-$^{14}$C-L-histidine. Two hours after the labeled histidine injection the animals are sacrificed, and the amount of radioactive histamine present in the glandular part of the stomach is determined as described by K. M. Mole and D. M. Shepherd, J. Pharm. Pharmac. 25, 609–613 (1973).

In addition to being useful pharmacological agents, the compounds of this invention wherein R is hydrogen are useful as intermediates for the preparation of cephalosporin derivatives of the following general Formula II which are useful as antibiotics.

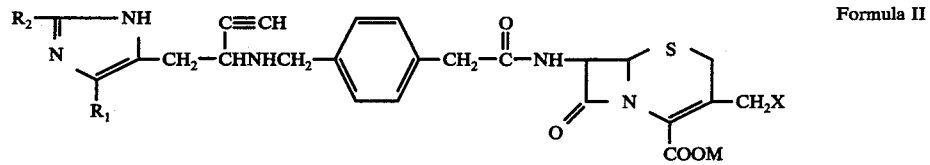

Formula II

In the above general Formula II X is hydrogen, acetoxy; M is hydrogen or a negative charge; $R_1$ and $R_2$ have the meanings defined in general Formula I.

The compounds of general Formula II and the pharmaceutically acceptable salts and individual optical isomers thereof are novel compounds useful as antibiotics and can be administered in a manner similar to that of many well known cephalosporin derivatives, for example, cephalexin, cephalothin, or cephaloglycine. The compounds of general Formula II and pharmaceutically acceptable salts and isomers thereof can be administered alone or in the form of pharmaceutical preparations either orally or parenterally and topically to warm blooded animals, that is, birds and mammals, for example, cats, dogs, bovine cows, sheep, horses and humans. For oral administration the compounds can be administered in the form of tablets, capsules or pills or in the form of elixirs or suspensions. For parenteral administration, the compounds may best be used in the form of a sterile aqueous solution which may contain other solutes, for example, enough saline or glucose to make the solution isotonic. For topical administration the compounds of general Formula II, salts and isomers thereof may be incorporated into creams or ointments.

Illustrative examples of bacteria against which the compounds of general Formula II and the pharmaceutically acceptable salts and individual optical isomers thereof are active are *Staphylococcus aureus, Salmonella schotmuehleri, Klebsiella pneumoniae, Diplococcus pneumoniae* and *Streptococcus pyogenes.*

Illustrative pharmaceutically acceptable non-toxic inorganic acid addition salts of the compounds of general Formula II are mineral acid addition salts, for example, hydrogen chloride, hydrogen bromide, sulfates, sulfamates, phosphate, and organic acid addition salts are, for example, maleate, acetate, citrate, oxalate, succinate, benzoate, tartrate, fumarate, malate and ascorbate. The salts can be formed by conventional means.

Illustrative examples of cephalosporin derivatives as represented by general Formula II are 7-[[2-[4-[1-acetylene-2-(4-imidazolyl)ethylaminomethyl]phenyl]acetyl]-amino]-3-acetyloxymethyl-8-oxo-5-thia-1-azabicyclo[4.2.0]-oct-2-ene-2-carboxylic acid, 7-[[2-[4-[1-acetylene-2-[5-(4-fluoro)imidazolyl]ethylaminomethyl]-phenyl]acetyl]amino]-3-acetyloxymethyl-8-oxo-5-thia-1-azabicyclo[4.2.0]oct-2-ene-2-carboxylic acid and 7-[[2-[4-[1-acetylene-2-[4-(2,5-dimethyl)imidazolyl]ethylaminomethyl]phenyl]acetyl]amino]-3-acetyloxymethyl-8-oxo-5-thia-1-azabicyclo[4.2.0]oct-2-ene-2-carboxylic acid.

The preparation of the compounds of general Formula II is described hereinafter.

The compounds of general Formula I wherein R is hydrogen are prepared by reacting an appropriately substituted N-tosyl-5-imidazolylacetaldehyde of the formula

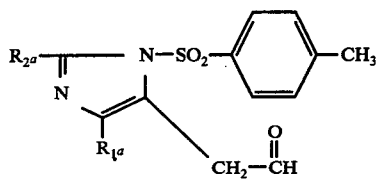

Formula III wherein each of $R_1a$ and $R_2a$ is hydrogen, halogen selected from fluorine, chlorine, bromine and iodine or a straight or branched lower alkyl group of from 1 to 4 carbon atoms and may be the same or different with the proviso that when both $R_1$ and $R_2$ are halogen $R_1$ and $R_2$ are the same, with a metal acetylide of the formula HC≡CM' wherein M' is sodium lithium or MgX' wherein X' is chlorine or bromine or with a complex of lithium acetylide/ethylenediamine in a solvent such as liquid ammonia, dimethylsulfoxide or an ether, for example, tetrahydrofuran, dioxane, diethylether or dimethoxyethane at a temperature of about −78° C to 25° C for about 1 minute to 12 hours, preferably 1 hour to give the corresponding N-tosyl-1-acetylene-2-imidazol-5-ylethanol. When sodium or lithium acetylide are employed liquid ammonia is the preferred solvent. When lithium acetylide is employed ether solvents are also preferred. Ether solvents are preferred when magnesium halide is employed with preferred reaction temperatures of about 0° to 25° C. When the complex lithium acetylide/ethylenediamine is employed the preferred solvent is dimethylsulfoxide with a temperature of about 25° C and time of about 1 to 12 hours.

The N-tosyl-1-acetylene-2-imidazol-5-ylethanol is treated with phthalimide, triphenylphosphine and diethyldiazodicarboxylate in ethers such as tetrahydrofuran, diethyl ether or dioxane for about 1 to 12 hours at about 25° to 50° C to afford the corresponding 1-phthalimido derivative which is treated with hydrazine hydrate in a lower alcohol solvent such as methanol or ethanol for about 1 to 6 hours at about 25° to 50° C followed by treatment with acid, for example, 6 N HCl, for 1 to 10 hours at 100° C. Alternatively the N-tosyl-1-acetylene-2-imidazol-5-ylethanol is treated with p-toluenesulfonyl chloride or mesyl chloride in a solvent such as an ether, for example, diethyl ether, dioxane or tetrahydrofuran, methylene chloride or chloroform in the presence of an organic amine such as pyridine or triethylamine, which may also serve as the solvent at a temperature of about 0° to 25° C for about 1 to 24 hours, preferably 12 hours; or with phosphorus trichloride in carbon tetrachloride, triphenylphosphine in carbon tetrachloride or carbon tetrabromide, or phosphorus tribromide, thionyl chloride or phosphorus pentachloride optionally in the presence of a solvent such as, an ether, for example, tetrahydrofuran, dioxane or diethyl ether, chloroform, methylene chloride, or benzene for about 1 to 24 hours at a temperature of about 0° to 80° C, preferably about 25° C followed by treatment with sodium amide and lithium amide in ammonia at about −78° to −30° C for about 1 to 6 hours and removal of the tosyl protecting group by treatment with 6 N hydrochloric acid for 2 to 10 hours at about 100° C.

The compounds of general formula III are known in the art or can be prepared by procedures known in the art, for example, by treating the appropriately substituted histidine derivative with sodium hypochlorite in water at about 0° to 25° C for about 1 to 6 hours. The chloroamino acid without isolation is added to hot aqueous acid and undergoes decarboxylation to the aldehyde on standing from 1 to 24 hours at about 25° C or upon heating at about 30° C to 100° C for about 1 to 3 hours. The thus obtained appropriately substituted imidazolyl acetaldehydes are treated in ethers such as tetrahydrofuran or diethyl ether, dichloromethane or chloroform with a base such as triethylamine or pyridine and p-toluenesulfonyl chloride at about 0° to 25° C for about 1 to 24 hours to afford the N-tosyl derivatives of Formula III.

The appropriately substituted histidine derivatives used as starting materials to prepare the compounds of general Formula III are known in the art or may be obtained by procedures known in the art, for example, as illustrated in the specific examples contained herein.

The compounds of general Formula I wherein R is alkylcarbonyl wherein the alkyl moiety is straight or branched and has from 1 to 4 carbon atoms are prepared by treating the corresponding derivatives wherein R is hydrogen with an acid halide of the formula

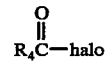

wherein halo is a halogen atom, for example, chlorine or bromine and $R_4$ is a straight or branched alkyl group having from 1 to 4 carbon atoms in water in the presence of a base such as sodium hydroxide or sodium borate at a temperature of from about 0° to 25° C for from about ½ hour to 6 hours.

The compounds of general Formula I wherein R is alkoxycarbonyl wherein the alkoxy moiety is straight or branched and has from 1 to 4 carbon atoms are prepared by treating the corresponding derivative wherein R is hydrogen with a halo alkylformate of the formula

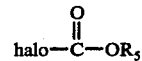

wherein halo is a halogen atom such as chlorine or bromine and $R_5$ is a straight or branched alkyl group having from 1 to 4 carbon atoms in water in the presence of a base such as sodium hydroxide or sodium borate at a temperature of from about 0° to 25° C for from about ½ hour to 6 hours.

The compounds of general Formula I wherein R is

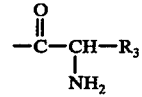

wherein $R_3$ is hydrogen, a straight or branched lower alkyl group of from 1 to 4 carbon atoms, benzyl or p-hydroxybenzyl are prepared by treating the corresponding derivative wherein R is hydrogen and the 1-imidazole nitrogen is protected with benzyloxycarbonyl or 2,4-dinitrophenyl with an acid of the formula

or a functional derivative thereof, such as the anhydride wherein the amino group is protected with a suitable blocking group such as benzyloxycarbonyl or tert-butoxycarbonyl and $R_3$ has the meaning defined hereinabove in an ether, such as, tetrahydrofuran or dioxane, methylene chloride or chloroform and in the presence of a dehydrating agent such as dicyclohexylcarbodiimide when the free acid is employed, at a temperature of from about 0° to 35° C for about 1 to 12 hours followed by acid and base hydrolysis to remove the protecting groups.

The individual optical isomers of the compounds of Formula I wherein R is H may be separated by using a (+) or (−) binaphthylphosphoric acid salt by the method of R. Viterbo et al., in Tetrahedron Letters 48, 4617 (1971). The individual optical isomers of compounds wherein R is other than H may be obtained as described herein for the racemic mixture only starting with the resolved amine.

As set forth hereinabove the compounds of general Formula I are useful as intermediates for the preparation of useful cephalosporin derivatives as described by general Formula II. The compounds of general Formula II are prepared by reacting a compound having the formula

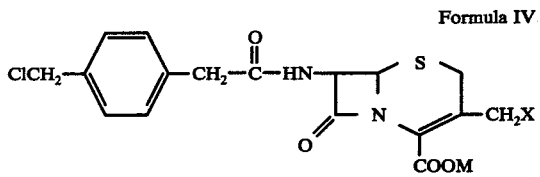

Formula IV wherein X and M have the meaning defined in general Formula II which compounds are prepared as described in U.S. Pat. No. 3,919,206 which patent is incorporated herein by reference thereto, with a compound of general Formula I wherein R is hydrogen and the 1-imidazole nitrogen is protected with a suitable blocking group such as tert-butoxycarbonyl. The reaction is generally carried out in a solvent, such as a lower alcohol, for example, methanol, ethanol, or isopropyl alcohol, or dimethylsulfoxide, dimethylformamide or aqueous mixtures of these solvents. The temperature of the reaction may vary from about 0° to 125° C and the reaction time may vary from about ½ hour to 24 hours. Following the reaction the amino protecting group is removed by acid hydrolysis and the cephalosporin products are isolated by conventional procedures.

The following Example 1 illustrates the use of a compound of general Formula I wherein R is hydrogen as a chemical intermediate in the preparation of a cephalosporin of Formula II.

EXAMPLE 1

7-[[2-[4-[1-acetylene-2-(4-imidazolyl)ethylaminomethyl]phenyl]acetyl]amino]-3-acetyloxymethyl-8-oxo-5-thia-1-azabicyclo[4.2.0]oct-2-ene-2-carboxylic acid A mixture of 1 g of 3-acetyloxymethyl-7-[[2-[4-(chloromethyl)phenyl]acetyl]amino]-8-oxo-5-thia-1-azabicyclo[4.2.0]oct-2-ene-2-carboxylic acid and 1 g of 1-acetylene-2-(5-imidazolyl)ethylamine wherein the 1-imidazole amino group is protected with tert-butoxycarbonyl in 50 ml of ethanol was stirred at 25° C for 24 hours after which the solvent is removed leaving a residue which is treated with mild acid and chromatographed on silica gel using benzeneacetone as the eluant to give 7-[[2-[4-[1-acetylene-2-(4-imidazolyl)ethylaminomethyl]phenyl]acetyl]amino]-3-acetyloxymethyl-8-oxo-5-thia-1-azabicyclo[4.2.0]oct-2-ene-2-carboxylic acid.

The following Examples 2 to 4 are representative of suitable pharmaceutical formulations employing compounds of the present invention.

EXAMPLE 2

An illustrative composition for hard gelatin capsules is as follows:

| (a) | 1-acetylene-2-[5-(4-fluoro)-imidazolyl]ethylamine | 20 mg |
|---|---|---|
| (b) | talc | 5 mg |
| (c) | lactose | 90 mg |

The formulation is prepared by passing the dry powders of (a) and (b) through a fine mesh screen and mixing them well. The powder is then filled into hard gelatin capsules at a net fill of 115 mg per capsule.

EXAMPLE 3

An illustrative composition for tablets is as follows:

| (a) | 1-acetylene-2-(5-imidazolyl)-ethylamine | 20 mg |
|---|---|---|
| (b) | starch | 43 mg |
| (c) | lactose | 45 mg |
| (d) | magnesium stearate | 2 mg |

The granulation obtained upon mixing the lactose with the compound (a) and part of the starch and granulated with starch paste is dried, screened, and mixed with the magnesium stearate. The mixture is compressed into tablets weighing 110 mg each.

EXAMPLE 4

An illustrative composition for an injectable suspension is the following 1 ml ampul for an intramuscular injection.

| | | Weight per cent |
|---|---|---|
| (a) | 1-acetylene-2-[5-(4-methyl)-imidazolyl]ethylamine | 1.0 |
| (b) | polyvinylpyrrolidone | 0.5 |
| (c) | lecithin | 0.25 |
| (d) | water for injection to make | 100.0 |

The materials (a)–(d) are mixed, homogenized and filled into 1 ml ampuls which are sealed and autoclaved 20 minutes at 121° C. Each ampul contains 10 mg per ml of novel compound (a).

The following examples further illustrate the compounds of the invention.

EXAMPLE 5

1-Acetylene-2-(5-imidazolyl)ethylamine dihydrochloride

A. To sodium acetylide, prepared from 2.3 g (100 mM) of sodium and 200 ml of ammonia is added 10.8 g (45 mM) of 2-(1-tosylimidazol-5-yl)acetaldehyde, and 10 minutes later ammonium chloride is added and the ammonia allowed to evaporate. The remaining residue is triturated with ether, and the ether solution filtered and evaporated to give 1-acetylene-2-(1-tosylimidazol-5-yl)ethanol.

B. To a solution of 5.8 g (20 mM) of the 1-tosylimidazole derivative in 20 ml of ether containing 2.2 g (20 mM) of triethylamine at 0° C is added 3.8 g (20 mM) of p-tosylchloride at 0° C. The solution is maintained at 0° C for 10 minutes, then filtered and the filtrate is added directly to a solution of 0.76 g (20 mM) of sodium amide in 200 ml of ammonia. The ammonia is allowed to evaporate and the remaining residue is treated with water and extracted with ether. The ether solution is dried and evaporated to give 1-acetylene-2-(1-tosylimidazol-5-yl)ethylamine which is purified by recrystallization from petroleum ether. 2.0 g (6.7 mM) of 1-acetylene-2-(1-tosylimidazol-5-yl)-ethylamine is refluxed with 25 ml of concentrated hydrochloric acid for 6 hours. The solution is washed with ether then concentrated to dryness and the resulting residue is recrystallized from isopropyl alcohol to give 1-acetylene-2-(5-imidazolyl)ethylamine dihydrochloride.

EXAMPLE 6

2-(1-Tosylimidazol-5-yl)acetaldehyde

A solution of 1.46 g (10 mM) of 2-(5-imidazolyl)-acetaldehyde HCl in 20 ml of dichloromethane is treated with 2.01 g (20 mM) of triethylamine and 1.9 g of p-toluenesulfonyl chloride at 25° C for about 16 hours after which the solution is washed with 3 N hydrochloric acid, water, sodium bicarbonate and water then dried and evaporated to afford 2-(1-tosylimidazol-5-yl)acetaldehyde upon recrystallization from ethyl acetate.

EXAMPLE 7

1-Acetylene-2-(5-imidazolyl)ethylamine dihydrochloride

A mixture of 2.9 g (10 mM) of 1-acetylene-2-(1-tosylimidazol-5-yl)ethanol, prepared in Example 5, 2.62 g (10 mM) of triphenylphosphine, 1.74 (10 mM) of diethyldiazodicarboxylate and 1.50 g (10 mM) of phthalimide in 200 ml of tetrahydrofuran is heated at reflux for 6 hours then concentrated to about 30 ml. On cooling to 0° C the resulting precipitate is collected to afford 1-acetylene-1-phthalimido-2-(N-tosylimidazol-5-yl)ethane, 2.0 g.

A solution of 2.0 g (4.8 mM) of the above obtained phthalimide derivative in 50 ml of ethanol is treated with 300 mg of hydrazine hydrate. The mixture is heated to reflux for 2 hours then the solvent is evaporated. The residue is treated with 20 ml of 10% aqueous potassium hydroxide and extracted well with dichloromethane. Evaporation of the organic phase affords 1-acetylene-2-(imidazol-5-yl)ethylamine 2.0 g of which is refluxed with 25 ml of concentrated hydrochloric acid for 6 hours. The solution is washed with ether then concentrated to dryness. The resulting residue is recrystallized from isopropyl alcohol to give 1-acetylene-2-(5-imidazolyl)ethylamine hydrochloride.

EXAMPLE 8

2-(4-Fluoro-5-imidazolyl)acetaldehyde hydrochloride

To 1.7 g (10 mM) of 4-fluorohistidine in 35 ml of water is added 10 ml of 1 M hydrochloric acid. The solution is cooled to 0° C then treated with 10 ml of a 1 M sodium hypochlorite. This solution is then added dropwise to water (50 ml) containing 15 ml of 1M hydrochloric acid at 90° C. On completion of the addition the solvent is evaporated under reduced pressure and the resulting solid is triturated with ethanol, filtered and the filtrate evaporated to give 2-(4-fluoro-5-imidazolyl)acetaldehyde hydrochloride.

EXAMPLE 9

2-Fluoro-4-methylhistidine

4-Methylhistidine methyl ester (free base) (10 g) is added to 35 ml of trifluoroacetic anhydride at −10° C. The mixture is stirred at 25° C for 5 hours, then the solvent is removed under reduced pressure. Water (50 ml) is added then removed in vacuo, this procedure being repeated 3 times, followed by a similar treatment with ethanol. The residue is recrystallized from ethyl acetate-ether to afford α-N-trifluoroacetyl-4-methylhistidine methyl ester as the trifluoroacetate salt.

A solution of 1.44 g (200 mM) of $NaNO_2$ in 20 ml of water at 0° C is added to a solution of 2.44 g (0.02 mole) of p-bromoaniline in 300 ml of 2.3 N HCl at 0° C. After 40 minutes at 0° C the resulting solution of the diazonium salt is added to a solution of α-N-trifluoroacetyl-4-methyl histidine methyl ester (5.5 g, 0.1 M, from the trifluoroacetate salt) in 200 ml of 0.2 M aqueous sodium carbonate. After 2 hours at 0° C the orange precipitate (6.0 g) is collected and dried, then suspended in 200 ml of ethanol containing 0.5 g of platinum oxide and subjected to catalytic hydrogenation (25° C, 40 psi Paar bomb) overnight after which the catalyst is filtered off and the solvent evaporated. The residue is treated with 100 ml of water, filtered and washed with ether. The aqueous layer is evaporated and the residue recrystallized from ethanol-ether to afford α-N-trifluoroacetyl-2-amino-4-methyl-histidine methyl ester.

To 100 ml of 50% aqueous $HBF_4$ at −10° C is added α-N-trifluoroacetyl-2-amino-4-methylhistidine methyl ester (2.5 g, 8.6 mM), followed by $NaNO_2$ (0.8 g, 12 mM) in 5 ml of water. This solution is diluted with 100 ml of cold $HBF_4$ and irradiated at 0° C with a Hanovia 450-W mediumpressure mercury vapor lamp, equipped with a Corex filter, in a quartz immersion well. After 1 hour irradiation time the reaction mixture is neutralized to pH 6 with cold concentrated sodium hydroxide, then extracted with ethylacetate. The ethyl acetate solution is concentrated to afford an oily residue which is treated with 15 ml of 0.5 M sodium hydroxide for 4 hours at 25° C. After neutralization the solution is applied to an Amberlite 120 H+ resin, and the product eluted with $NH_4OH$ (1 M). Evaporation of the ammonia and recrystallization from methanol gives 2-fluoro-4-methylhistidine.

EXAMPLE 10

4-Fluoro-2-methylhistidine

2-Methylhistidine methyl ester (free base) (10 g) is added to 35 ml of trifluoroacetic anhydride at −10° C. The mixture is stirred at 25° C for 5 hours, then the solvent is removed under reduced pressure. Water (50 ml) is added and then removed in vacuo, this procedure being repeated 3 times, followed by a similar treatment with ethanol. The residue is recrystallized from ethyl acetate-ether to afford α-N-trifluoroacetyl-2-methylhistidine methyl ester as its trifluoroacetate salt.

A solution of 1.44 g (200 mM) of $NaNO_2$ in 20 ml of water at 0° C is added to a solution of 3.44 g (0.02 mole)

of p-bromoaniline in 100 ml of 2.3 N HCl at 0° C. After 40 minutes at 0° C the resulting solution of the diazonium salt is added to a solution of α-N-trifluoroacetyl-4-methyl histidine methyl ester (5.5 g, 0.1 M, from the trifluoroacetate salt) in 200 ml of 0.2 M aqueous sodium carbonate. After 2 hours at 0° C the orange precipitate (6.0 g) is collected and dried, then suspended in 200 ml of ethanol containing 0.5 g platinum oxide and subjected to catalytic hydrogenation (25° C, 40 psi Paar bomb) overnight. The catalyst is filtered off and the solvent evaporated. The residue is treated with 100 ml of water, filtered and washed with ether. The aqueous layer is evaporated and the residue recrystallized from ethanol-ether to afford α-N-trifluoroacetyl-2-methyl-4-aminohistidine methyl ester.

To 100 ml of 50% aqueous $HBF_4$ at −10° C is added α-N-trifluoroacetyl-2-methyl-4-aminohistidine methyl ester (2.5 g, 8.6 mM), followed by $NaNO_2$ (0.8 g, 12 mM) in 5 ml of water. This solution is diluted with cold $HBF_4$ (100 ml) and irradiated at 0° C with a Hanovia 450-W medium-pressure mercury vapor lamp, equipped with a Corex filter, in a quartz immersion well. After 1 hour irradiation time the reaction mixture is neutralized to pH 6 with cold concentrated sodium hydroxide, then extracted with ethyl acetate. The ethyl acetate solution is concentrated to afford an oily residue which is treated with 15 ml of 0.5 M sodium hydroxide for 4 hours at 25° C. After neutralization the solution is applied to an Amberlite 120 $H^+$ resin, and the product eluted with $NH_4OH$ (1 M). Evaporation of the ammonia and recrystallization from methanol gives 4-fluoro-2-methylhistidine.

EXAMPLE 11

2,4-Difluorohistidine

A solution of 1.44 g (200 mM) of $NaNO_2$ in water (20 ml) at 0° C is added to a solution of p-bromoaniline (6.88 g, 0.04 M) in HCl (200 ml of 2.3 N) at 0° C. After 40 minutes at 0° C the resulting solution of the diazonium salt is added to a solution of α-N-benzoylhistidine methyl ester (5.5 g, 0.1 M) in aqueous $Na_2CO_3$ (400 ml of 0.2 M). After 2 hours at 0° C the orange precipitate (12.0 g) is collected and dried, then suspended in 400 ml of ethanol containing 0.5 g of platinum oxide and subjected to catalytic hydrogen (25° C, 40 psi Paar bomb) overnight. The catalyst is filtered off and the solvent evaporated. The residue is treated with 200 ml of water, filtered and washed with ether. The aqueous layer is evaporated and the residue recrystallized from ethanol-ether to afford α-N-benzoyl-2,4-diaminohistidine methyl ester.

To 100 ml of 50% aqueous $HBF_4$ at −10° C is added α-N-benzoyl-2,4-diamino histidine methyl ester (2.5 g), followed by $NaNO_2$ (1.6 g, 24 mM) in water (10 ml). This solution is diluted with cold $HBF_4$ (200 ml) and irradiated at 0° C with a Hanovia 450-W medium-pressure mercury vapor lamp, equipped with a Corex filter, in a quartz immersion well. After 1 hour irradiation time the reaction mixture is neutralized to pH 6 with cold concentrated sodium hydroxide then extracted with ethyl acetate. The ethyl acetate solution is concentrated to afford an oily residue which is treated wth NaOH (0.5 M, 30 ml) for 14 hours at 25° C. After neutralization the solution is applied to an Amberlite 120 $H^+$ resin, and the product eluted with $NH_4OH$ (1 M). Evaporation of the ammonia and recrystallization from methanol gives 2,4-difluorohistidine.

The 2-alkyl or 4-alkyl and the 2,4-dialkylhistidine derivatives employed herein are prepared from 5-hydroxymethylimidazole substituted at the 2 and/or 4-positions with an appropriate lower alkyl group by the general procedure described by K. Matsumoto et al., Agr. Biol. Chem. 38 (5), 1097 (1974). The 2,4-dialkyl-5-hydroxymethylimidazoles are prepared by hydroxymethylation of the 2,4-dialkylimidazole with formaldehyde by the general procedure of M. Masui et al., Chem. Pharm. Bull. 1974, 2359. The 4-alkyl-5-hydroxymethylimidazoles are similarly prepared according to the method described by Ewins, J. Chem. Soc. 99, 2052 (1911). The 2-alkyl-5-hydroxymethylimidazoles are prepared by hydroxymethylation of 1-benzyl-2-alkylimidazoles to give 1-benzyl-2-alkyl-4-hydroxymethylimidazoles according to E. F. Godefroi et al., Rec. Trav. Chim. Pays Bar 91, 1385 (1972). The N-benzyl group is subsequently removed using $Na/NH_3$ as described, for example, by R. G. Jones, J. Am. Chem. Soc. 71, 383 (1949).

EXAMPLE 12

2,4-Dichlorohistidine

To a solution of 1.6 g (24 mM) of sodium nitrite in 16 ml of concentrated sulfuric acid at 25° C is added 2.5 g (8.0 mM) of α-N-benzoyl-2,4-diaminohistidine in 20 ml of acetic acid at such a rate as to maintain the temperature below 35° C. This solution is then added with cooling to a solution of 10 g of cuprous chloride in 20 ml of concentrated hydrochloric acid. The combined solution is maintained at 25° C for 10 minutes then neutralized by careful addition of cold concentrated sodium hydroxide followed by extraction with ethyl acetate. The ethyl acetate extract is concentrated to afford an oily residue which is treated with 30 ml of 0.5 M sodium hydroxide for 14 hours at 25° C. After neutralization the solution is applied to an Amberlite 120 $H^+$ resin and eluting with 1 M ammonium hydroxide and evaporation of the ammonia affords 2,4-dichlorohistidine upon recrystallization from methanol.

When in the above procedure of Example 12 an appropriate amount of cuprous bromide is substituted for cuprous chloride and hydrobromic acid is used in place of hydrochloric acid, 2,4-dibromohistidine is obtained.

The 2,4-diiodohistidine compound [D. Mackay and D. M. Shepherd, Brit. J. Pharmacol. 15, 552 (1960)] is obtained from the diazonium salt, formed in situ in the procedure of Example 12, by pouring said salt into aqueous potassium iodide containing aqueous iodide.

When in the above procedure of Example 12 an appropriate amount of the α-N-benzoyl derivative of 2-amino-4-(lower)-alkylhistidine methyl ester, 2-(lower)alkyl-4-aminohistidine methyl ester, wherein the lower alkyl group has from 1 to 4 carbon atoms and is straight or branched, 2-aminohistidine or 4-aminohistidine is substituted for α-N-benzoyl-2,4-diaminohistidine the following compounds are obtained: 2-chloro-4-(lower)alkylhistidine, 2-(lower)alkyl-4-chlorohistidine, 2-chlorohistidine and 4-chlorohistidine, and when the procedure of Example 12 is further modified by substituting an appropriate amount of cuprous bromide for cuprous chloride and hydrobromic acid is substituted for hydrochloric acid the following compounds are obtained: 2-bromo-4-(lower)-alkylhistidine, 2-(lower)alkyl-4-bromohistidine, 2-bromohistidine and 4-bromohistidine.

The 2- or 4-diiodohistidine derivatives and the 2-iodo-4-(lower)alkyl- and the 4-iodo-2-(lower)alkylhistidine derivatives are obtained respectively from the 2- or 4- diazohistidine derivative and the 2-diazo-4-(lower)alkyl- and the 4-diazonium-2-(lower)alkylhistidine derivatives by pouring the appropriate diazonium derivative into aqueous potassium iodide containing aqueous iodide. The 2- or 4-diazohistidine derivative and the 2-diazonium-4-(lower)alkyl- and the 4-diazonium-2-(lower)alkylhistidine derivatives are formed in situ when in the procedure of Example 12 the α-N-benzoyl derivative of 2- or 4-aminohistidine, 2-amino-4-(lower)alkylhistidine or 4-amino-2-(lower)alkylhistidine is substituted respectively for α-N-benzoyl-2,4-diaminohistidine.

EXAMPLE 13

When in the procedure of Example 8 an appropriate amount of 2-fluoro-4-methylhistidine, 4-fluoro-2-methyl-histidine, 2,4-difluorohistidine, 2,4-dichlorohistidine, 4-chlorohistidine, 2,4-dibromohistidine or 2,4-diiodohistidine is substituted for 4-fluorohistidine, the following compounds are obtained:

2-(2-fluoro-4-methylimidazol-5-yl)acetaldehyde,
2-(4-fluoro-2-methylimidazol-5-yl)acetaldehyde,
2-(2,4-difluoroimidazol-5-yl)acetaldehyde,
2-(2,4-dichloroimidazol-5-yl)acetaldehyde,
2-(2,4-dibromoimidazol-5-yl)acetaldehyde, and
2-(2,4-diiodoimidazol-5-yl)acetaldehyde.

EXAMPLE 14

When in the procedure of Example 6 an appropriate amount of the acetaldehyde compounds obtained in Example 13 is substituted for 2-(5-imidazolyl)acetaldehyde the following compounds are obtained:

2-(2-fluoro-4-methyl-1-tosylimidazol-5-yl)acetaldehyde,
2-(4-fluoro-2-methyl-1-tosylimidazol-5-yl)acetaldehyde,
2-(2,4-difluoro-1-tosylimidazol-5-yl)acetaldehyde,
2-(2,4-dichloro-1-tosylimidazol-5-yl)acetaldehyde,
2-(2,4-dibromo-1-tosylimidazol-5-yl)acetaldehyde, and
(2,4-diiodo-1-tosylimidazol-5-yl)acetaldehyde.

EXAMPLE 15

When in the procedure of Example 5(A) an appropriate amount of the 1-tosyl derivatives prepared in Example 14 is substituted for 2-(1-tosylimidazol-5-yl)acetaldehyde the following compounds are obtained:

1-acetylene-2-(2-fluoro-4-methyl-1-tosylimidazol-5-yl)ethanol,
1-acetylene-2-(4-fluoro-2-methyl-1-tosylimidazol-5-yl)ethanol,
1-acetylene-2-(2,4-difluoro-1-tosylimidazol-5-yl)ethanol,
1-acetylene-2-(2,4-dichloro-1-tosylimidazol-5-yl)ethanol,
1-acetylene-2-(2,4-dibromo-1-tosylimidazol-5-yl)ethanol and
1-acetylene -2-(2,4-diiodo-1-tosylimidazol-5-yl)ethanol.

When an appropriate amount of the above obtained 1-acetylene ethanol derivatives is substituted for 2-(1-tosylimidazol-5-yl)ethanol in the procedure of Example 5(B) or in the procedure of Example 7 the following products are obtained:

1-acetylene-2-(2-fluoro-4-methylimidazol-5-yl)ethylamine dihydrochloride,
1-acetylene-2-(4-fluoro-2-methylimidazol-5-yl)ethylamine di-HCl,
1-acetylene-2-(2,4-difluoroimidazol-5-yl)ethylamine di-HCl,
1-acetylene-2-(2,4-dichloroimidazol-5-yl)ethylamine di-HCl,
1-acetylene-2-(2,4-dibromoimidazol-5-yl)ethylamine di-HCl and,
1-acetylene-2-(2,4-diiodoimidazol-5-yl)ethylamine di-HCl.

EXAMPLE 16

N-[1-Acetylene-2-(5-imidazolyl)ethyl]acetamide

A solution of 1.93 g (10 mM) of 1-acetylene-2-(5-imidazolyl)ethylamine dihydrochloride in 26 ml of 2 M sodium hydroxide solution is cooled to 5° C. To this solution is added simultaneously from two syringes 1 g (13 mM) of acetyl chloride and 5 ml of 2 M sodium hydroxide solution dropwise. After 2 hours the solution is neutralized by the addition of 16 ml of 1 M hydrochloric acid then evaporated to dryness. The residue is triturated with dichloromethane, filtered and evaporated to afford N-[1-acetylene-2-(5-imidazolyl)ethyl]acetamide which is recrystallized from ethyl acetate.

When in the above procedure an appropriate amount of ethyl chloroformate is substituted for acetyl chloride, ethyl N-[1-acetylene-2-(5-imidazolyl)ethyl]carbamate is obtained, and when an appropriate amount of benzyl chloroformate is substituted for acetyl chloride benzyl N-[1-acetylene-2-(5-imidazolyl)ethyl]carbamate is obtained.

EXAMPLE 17

N-[1-Acetylene-2-[5-(2-ethyl)imidazolyl]ethyl]-2-amino propionamide

To a solution of 2.69 g (10 mM) of N-[1-acetylene-3-[5-(2-ethyl)imidazolyl]ethyl]-2-benzylcarbamate in 20 ml of methylene chloride containing 1.1 g of triethylamine is added 1.70 g (10 mM) of benzyl chloroformate. After 2 hours at 25° C the solution is washed with water and 1 N hydrochloric acid then evaporated to afford the dicarbobenzoxy derivative. To this residue is added 30 ml of 100% (w/w) hydrogen bromide in dioxane and the mixture is allowed to stand at 25° C for 30 minutes after which 150 ml of ether is added. The resulting precipitate is filtered off and added to cold bicarbonate solution then rapidly extracted with dichloromethane. The dried organic phase is concentrated to afford 1-carbobenzoxy-5-[2-acetylene-2-aminoethyl]imidazole which is treated in 10 ml of dichloromethane with 1.6 g (7 mM) of N-carbobenzoxyalanine and 1.45 g (7 mM) of N,N'-dicyclohexylcarbodiimide for about 16 hours at 25° C. The mixture is then cooled to 0° C and filtered. The organic solution is washed with 1N hydrochloric acid and bicarbonate solution then dried and concentrated. The residue is treated with 30 ml of 100% (w/w) hydrogen bromide in dioxane for 30 minutes at 25° C. Addition of 150 ml of ether resulted in a precipitate of the hydrobromide which is filtered off and treated for about 16 hours with 50 ml of 1 N sodium hydroxide at 25° C. The resulting solution is adjusted to neutral pH and the product isolated from an Amberlite 120 H+ resin by elution with 2 M ammonia to yield N-[1-acetylene-2-[5-(2-ethyl)-imidazolyl]ethyl9 -2-aminopropionamide.

We claim:
1. A compound of the formula

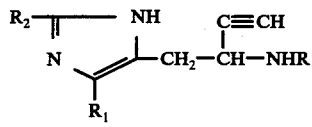

wherein R is hydrogen, alkylcarbonyl wherein the alkyl moiety has from 1 to 4 carbon atoms and is straight or branched, alkoxycarbonyl wherein the alkoxy moiety has from 1 to 4 carbon atoms and is straight or branched or

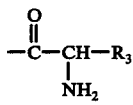

wherein $R_3$ is hydrogen, a straight or branched lower alkyl group of from 1 to 4 carbon atoms, benzyl or p-hydroxybenzyl; each of $R_1$ and $R_2$ is hydrogen, halogen selected from fluorine, chlorine, bromine and iodine, or a straight or branched lower alkyl group of from 1 to 4 carbon atoms and may be the same or different with the proviso that when both of $R_1$ and $R_2$ are halogen $R_1$ and $R_2$ are the same; and pharmaceutically acceptable salts and individual optical isomers thereof.

2. A racemic mixture of a compound of claim 1.

3. A compound of claim 1 wherein R is hydrogen or alkylcarbonyl wherein the alkyl moiety has from 1 to 4 carbon atoms and is straight or branched.

4. A compound of claim 1 wherein R is hydrogen.

5. A compound of claim 1 wherein each of $R_1$ and $R_2$ is hydrogen, fluorine, chlorine or methyl.

6. A compound of claim 1 wherein each of $R_1$ and $R_2$ is hydrogen.

7. A compound of claim 1 which is 1-acetylene-2-(5-imidazolyl)ethylamine or a pharmaceutically acceptable salt thereof.

8. A compound of claim 1 which is 1-acetylene-2-[5-(2-fluoro)imidazolyl]ethylamine or a pharmaceutically acceptable salt thereof.

9. A compound of claim 1 which is 1-acetylene-2-[5-(4-methyl)imidazolyl]ethylamine or a pharmaceutically acceptable salt thereof.